(12) United States Patent
Larson

(10) Patent No.: US 9,513,272 B2
(45) Date of Patent: Dec. 6, 2016

(54) METHOD AND APPARATUS FOR MEASURING DRILLING FLUID PROPERTIES

(71) Applicant: National Oilwell Varco, L.P., Houston, TX (US)

(72) Inventor: Thomas Robert Larson, Montgomery, TX (US)

(73) Assignee: National Oilwell Varco, L.P., Houston, TX (US)

( * ) Notice: Subject to any disclaimer, the term of this patent is extended or adjusted under 35 U.S.C. 154(b) by 450 days.

(21) Appl. No.: 14/203,854

(22) Filed: Mar. 11, 2014

(65) Prior Publication Data

US 2014/0262516 A1    Sep. 18, 2014

Related U.S. Application Data

(60) Provisional application No. 61/794,336, filed on Mar. 15, 2013.

(51) Int. Cl.
*G01N 33/28* (2006.01)
*G01N 11/08* (2006.01)
*G01N 11/00* (2006.01)
*E21B 49/08* (2006.01)

(52) U.S. Cl.
CPC .......... *G01N 33/2823* (2013.01); *G01N 11/08* (2013.01); *E21B 2049/085* (2013.01); *G01N 2011/0026* (2013.01)

(58) Field of Classification Search
CPC ................................. G01N 33/2823
USPC ...................................... 73/152.18
See application file for complete search history.

(56) References Cited

U.S. PATENT DOCUMENTS

| | | |
|---|---|---|
| 1,641,673 A | 9/1927 | Hall |
| 3,074,266 A | 1/1963 | Sadler et al. |
| 3,462,596 A | 8/1969 | Saunders |
| 4,059,987 A | 11/1977 | Dowling et al. |

(Continued)

FOREIGN PATENT DOCUMENTS

| | | |
|---|---|---|
| CN | 1773245 | 5/2006 |
| CN | 102374960 | 3/2012 |

(Continued)

OTHER PUBLICATIONS

PCT International Search Report and Written Opinion dated Feb. 9, 2015, for International Application No. PCT/US2014/042639, 13 pages.

(Continued)

*Primary Examiner* — Michael A Lyons
*Assistant Examiner* — Jean Morello
(74) *Attorney, Agent, or Firm* — Amerson Law Firm, PLLC (57) ABSTRACT

As system for measuring drilling fluid properties includes a capillary rheometer that is adapted to measure viscosity parameters of drilling fluid. The capillary rheometer includes a feed chamber, the feed chamber having a cavity, at least a first drain port for draining fluid out of the cavity, a double wall defining an annulus that opens to the cavity, and a feed port in an outer portion of the double wall that is in fluid communication with the annulus. The capillary rheometer also includes at least a first capillary tube coupled to at least the first drain port. Additionally, the disclosed system further includes a pump that is adapted to pump fluid to the feed port.

42 Claims, 6 Drawing Sheets

(56) References Cited

U.S. PATENT DOCUMENTS

| | | | |
|---|---|---|---|
| 4,301,400 A | 11/1981 | Paap | |
| 4,499,418 A | 2/1985 | Helms et al. | |
| 4,587,837 A | 5/1986 | Newbould | |
| 4,812,739 A | 3/1989 | Swanson | |
| 4,862,060 A | 8/1989 | Scott et al. | |
| 4,891,969 A | 1/1990 | Wayland et al. | |
| 5,056,358 A | 10/1991 | Laskowski et al. | |
| 5,625,293 A | 4/1997 | Marrelli et al. | |
| 5,652,376 A | 7/1997 | Deleeuw et al. | |
| 6,076,049 A | 6/2000 | Lievois et al. | |
| 6,412,337 B1 | 7/2002 | Arzate et al. | |
| 6,578,409 B1 | 6/2003 | Zhou et al. | |
| 6,831,470 B2 | 12/2004 | Xie et al. | |
| 7,908,930 B2 | 3/2011 | Xie et al. | |
| 2006/0186340 A1 | 8/2006 | Lievois et al. | |
| 2010/0139387 A1 | 6/2010 | Jamison et al. | |
| 2013/0025359 A1 | 1/2013 | Cartellieri et al. | |
| 2014/0005957 A1 | 1/2014 | Pihlaja | |

FOREIGN PATENT DOCUMENTS

| | | | |
|---|---|---|---|
| CN | 202216888 | 5/2012 | |
| CN | 202216888 U * | 5/2012 | ............. G01N 11/08 |
| DE | 2636060 | 2/1978 | |
| EP | 0007759 | 2/1980 | |
| FR | 1090706 A | 4/1955 | |
| WO | 2011073789 | 6/2011 | |
| WO | 2012061872 | 5/2012 | |

OTHER PUBLICATIONS

"Choke Valves | Enggcyclopedia", Mar. 1, 2012, retrieved on Jan. 22, 2015 from the Internet, URL: http://www.enggcyclopedia.com/2012/03/choke-valves/.

Thermie Integrated Systems Brochure, 1993/94.

Twin Bore Capillary Rheometer R 6000, Qualitest International Inc., Oct. 2010.

PCT Partial International Search, Annex to Invitation to Pay Additional Fees dated Jun. 16, 2014, for International Application No. PCT/US2014/024077, 6 pages.

Kawatra and Bakshi, "On-Line Viscometry in Particulate Processing," Mineral Processing and Extractive Metallurgy Review, 14:249-73, 1995.

* cited by examiner

METHOD AND APPARATUS FOR MEASURING DRILLING FLUID PROPERTIES

BACKGROUND

1. Field of the Disclosure

The present disclosure is generally directed to drilling fluids that are used during drilling operations for oil and gas wells, and in particular, to methods and apparatuses for analyzing the properties of such drilling fluids.

2. Description of the Related Art

Drilling fluid, or "mud," is a multicomponent fluid specially formulated to perform various functions during drilling of an oil or gas well. Examples of such functions include cooling the drill bit, lubricating and sealing the wall of the well, providing hydrostatic pressure in the well annulus to prevent formation fluid influx, clearing away drilled solids from the drill bit, and returning drilled solids to the surface. Circulation of the drilling fluid through the well typically involves pumping the drilling fluid down the bore of a drill string in the well, whereby the drilling fluid jets through nozzles in a drill bit at the end of the drill string into the bottom of the well. At the bottom of the well, the drilling fluid commingles with drilled solids and possibly other materials in the well such as gases and returns to the surface with the entrained materials. The return path is typically in an annulus between the wall of the well and the drill string. In dual bore drilling, the return path may be in the drill string. At the surface, a series of actions is taken to rid the drilling fluid of the entrained materials so that the drilling fluid can be pumped into the well again.

Drilling fluid is generally an aqueous or non-aqueous suspension of one or more materials. The suspension medium may be water or brine, oil, or synthetic fluid combined with various chemical additives. The added materials can be minerals, such as barite or bentonite, or synthetic polymers in particulate form. At various stages of removing the entrained materials, it is important to analyze the properties of the drilling fluid in order to ascertain that the drilling fluid has the proper composition and rheology to achieve desired functions. The drilling fluid properties measured are typically density, viscosity, and solids content. Currently, drilling fluid properties are measured using at least four devices, such as a mud balance, a Marsh funnel, a rotating cylinder viscometer, and a mud retort. The measurements are customarily made manually in that a technician collects a sample of drilling fluid, places the sample in the device, reads some type of physical indicator by eye, and records the measurement. These manual measurements are prone to errors that may prove costly in a drilling process.

A mud balance is used to measure drilling fluid density. To measure drilling fluid density, a cup is overfilled with a sample of the drilling fluid while placing a lid over the sample in such a way that there are no bubbles in the volume of drilling fluid remaining in the cup. The cup is then placed at one end of a graduated beam having a bubble level. A slider weight is moved along the length of the beam until the bubble level indicates that the beam is level. The position of the slider weight along the length of the beam indicates the density of the drilling fluid. The accuracy of the density measurement depends on how accurately the technician can read the bubble level and the position of the slider weight. Most mud balance beams are graduated in increments of 0.1 pounds/gallon.

A Marsh funnel is used to measure drilling fluid viscosity. To measure drilling fluid viscosity, the funnel is held vertically while plugging the bottom of the funnel. The drilling fluid is then poured into the funnel through a filter, e.g., a 10 Mesh screen. The filter will prevent solids that can clog the funnel from entering the funnel. When a desired amount of the drilling fluid has been poured into the funnel, the bottom of the funnel is unplugged to allow the drilling fluid to flow into a graduated container. The technician uses a stopwatch to record the time needed for a predetermined volume of the drilling fluid to be released from the funnel into the container. The accuracy of the viscosity measurement depends on the ability of the technician to accurately read the volume of drilling fluid released into the container and to accurately start and stop the stopwatch.

In the Marsh funnel method, filtering of the drilling fluid actually changes the drilling fluid so that the viscosity measured is more an apparent viscosity than a true viscosity. Also, particles in the drilling fluid may segregate inside the funnel while the bottom of the funnel is plugged, which may lead to variations in flow rate out of the funnel that would not be accounted for by merely measuring time and the amount of fluid released into the container. The range of application of the device is limited to those fluids that continue to flow freely as the level inside the funnel drops to very low values. Other fluids not having this property may result in clogging of the funnel by surface tension forces.

A rotating cylinder viscometer is also used to measure drilling fluid viscosity. A typical rotating cylinder viscometer includes two concentric cylinders. The inner cylinder is often referred to as bob and is suspended on a torque measuring device. To measure drilling fluid viscosity, drilling fluid is poured into a chamber through a filter, e.g., a 200 Mesh screen. The filter will prevent solids that can lodge in between the concentric cylinders from entering the chamber. The cylinders are then submerged in the drilling fluid in the chamber, and the outer cylinder is rotated at various rotational speeds while the bob is held stationary. The force necessary to shear the fluid between the cylinders is read from the torque measuring device that holds the bob stationary. Viscosity is estimated using an expression that is a function of the shear torque, the geometry of the cylinders, the angular velocity of the outer cylinder, and the immersion depth of the inner cylinder or bob in the drilling fluid. The rotating cylinder viscometer provides additional value over the Marsh funnel in that multiple rotational speeds correspond to multiple strain rates, which allows non-Newtonian behavior to be recorded for the drilling fluid.

The accuracy of the viscosity measurements made by the rotating cylinder viscometer depends on the accuracy of the rotational speed of the outer cylinder, on the accuracy of the reading of the indicator of the torque measuring device, and on the depth of immersion of the cylinders. In older versions of the device, a hand crank is used to rotate the outer cylinder. The normal procedure calls for turning the hand crank very evenly through a gearbox that allows for several specific speeds, if the handle is turning at a constant rotational speed. However, this constant rotational speed has to be achieved by hand, which can be very difficult. A more modern version of the device uses a motor to drive the outer cylinder at precisely correct rotational speeds, which results in better precision. The viscosity measurements made by the rotating cylinder viscometer are affected by filtering of the drilling fluid received in the chamber, i.e., the actual drilling fluid measured is different from the original drilling fluid that contained the solids removed by the filtering. There is also the possibility of particles settling within the chamber while the viscosity measurements are being made. Particle settling can introduce errors to the measured shear torque.

A mud retort is used to measure many drilling fluid properties, e.g., the density of the drilling fluid, the density of the drilled solids, and the overall solids content of the drilling fluid. To make measurements with the mud retort, a known volume of fluid is heated in a retort chamber, typically to a temperature of over 900° F. Steam and vaporized oil exit the chamber and immediately pass through a condenser that returns the vapors to liquids and delivers the liquids to a graduated cylinder. The volumes of the liquids read from the cylinder are subtracted from the known volume to determine a volume of the solids in the drilling fluid. The mass of the solids can be determined, e.g., on a digital scale. The volume and mass of the solids are used to determine the specific gravity of the solids.

The present disclosure is directed to various methods and apparatuses for measuring the properties of drilling fluids that may address, at least in part, some of the above-described problems associated with prior art devices and methods that are used to evaluate drilling fluid properties.

SUMMARY OF THE DISCLOSURE

The following presents a simplified summary of the present disclosure in order to provide a basic understanding of some aspects disclosed herein. This summary is not an exhaustive overview of the disclosure, nor is it intended to identify key or critical elements of the subject matter disclosed here. Its sole purpose is to present some concepts in a simplified form as a prelude to the more detailed description that is discussed later.

The present disclosure is generally directed to various methods and apparatuses for analyzing the properties of drilling fluids that may be used during oil and gas well drilling operations. In one illustrative embodiment, a system for measuring drilling fluid properties is disclosed that includes a capillary rheometer that is adapted to measure viscosity parameters of drilling fluid. The capillary rheometer includes, among other things, a feed chamber, the feed chamber having a cavity, at least a first drain port for draining fluid out of the cavity, a double wall defining an annulus that opens to the cavity, and a feed port in an outer portion of the double wall that is in fluid communication with the annulus. The capillary rheometer also includes at least a first capillary tube coupled to at least the first drain port. Additionally, the disclosed system further includes a pump that is adapted to pump fluid to the feed port.

In another illustrative embodiment, a method of measuring drilling fluid properties is disclosed that includes, among other things, pumping a drilling fluid into a feed chamber of a capillary rheometer, and controlling a delivery rate of the drilling fluid into the feed chamber during the pumping such that a first strain rate is imparted to the drilling fluid flowing through the capillary rheometer. The method further includes draining the drilling fluid through at least one drain port of the feed chamber and into an inlet of a capillary tube coupled to the at least one drain port, determining a flow rate and pressure drop of the drilling fluid flowing through the capillary rheometer for the first strain rate, and determining a viscosity of the drilling fluid from the flow rate and the pressure drop.

BRIEF DESCRIPTION OF THE DRAWINGS

The disclosure may be understood by reference to the following description taken in conjunction with the accompanying drawings, in which like reference numerals identify like elements, and in which.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention.

DETAILED DESCRIPTION

Various illustrative embodiments of the present subject matter are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present subject matter will now be described with reference to the attached figures. Various systems, structures and devices are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

In the following detailed description, various details may be set forth in order to provide a thorough understanding of the various exemplary embodiments disclosed herein. However, it will be clear to one skilled in the art that some illustrative embodiments of the invention may be practiced without some or all of these such various disclosed details. Furthermore, features and/or processes that are well-known in the art may not be described in full detail so as not to unnecessarily obscure the disclosed subject matter. In addition, like or identical reference numerals may be used to identify common or similar elements.

Figure 1:
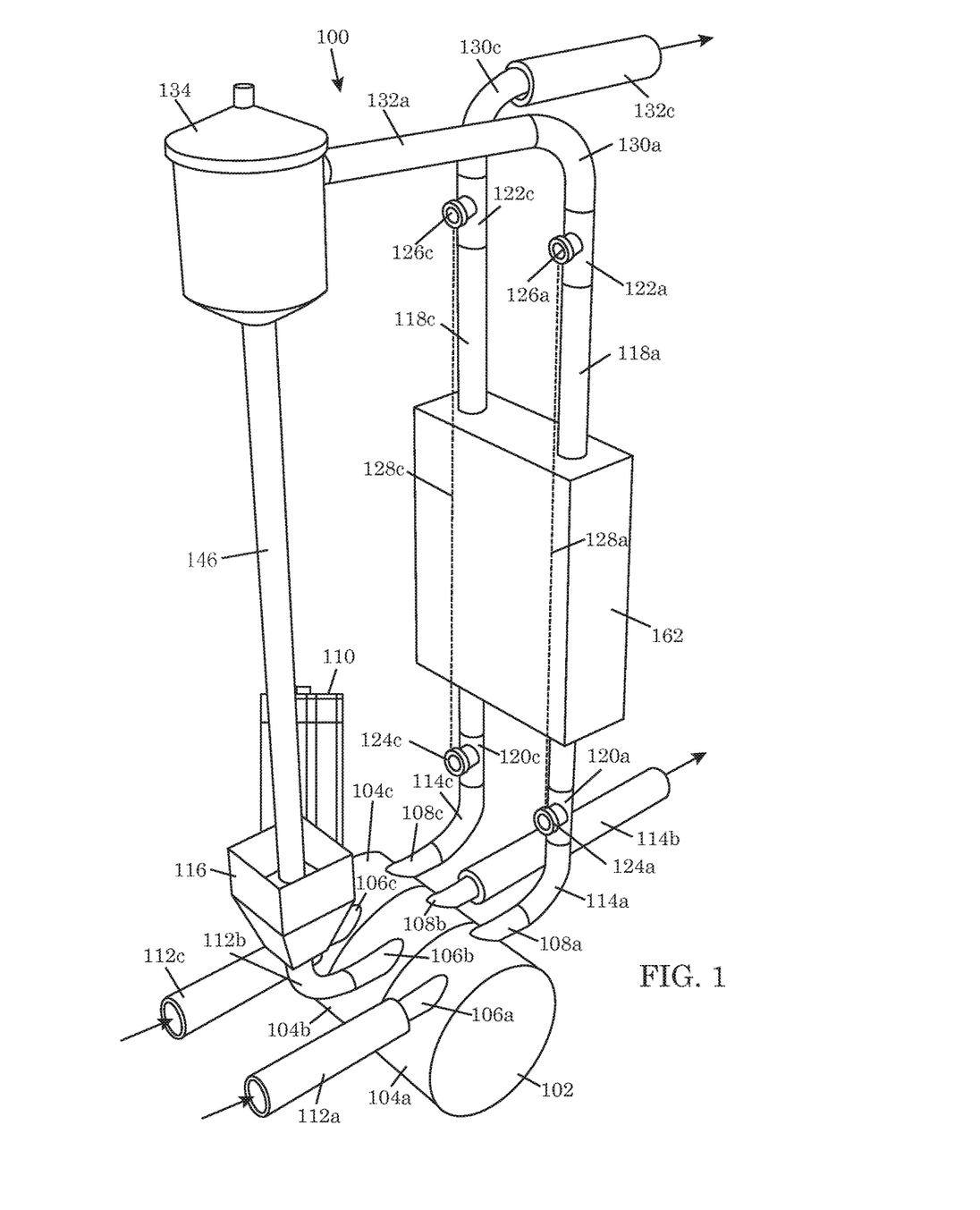
FIG. 1 shows a system for measuring drilling fluid properties.

FIG. 1 shows an illustrative system 100 that may be used to measure drilling fluid properties. In certain embodiments, the system 100 may include a pump module 102, which in turn may include a plurality of pump units, such as, for example, pump units 104a, 104b, 104c with associated suction ports 106a, 106b, 106c and discharge ports 108a, 108b, 108c. Although three pump units are shown in the exemplary pump module 102 of FIG. 1, the pump module 102 may have less than three or more than three pump units in other embodiments. Each of the pump units 104a, 104b, 104c is a complete pump and may have any pump design known in the art for pumping fluid, e.g., drilling fluid. As shown in the illustrated embodiment of FIG. 1, the pump units 104a, 104b, 104c may be integrated into a single body and coupled to a single drive motor 110. In other embodiments, the pump unit 104a, 104b, 104c may be separate and coupled to separate drive motors. Preferably, the drive motor 110 is a variable speed drive motor that is adapted to receive control signals from an external control system (see, FIG. 3).

In one or more embodiments, the pump units 104a, 104b, 104c may be positive-displacement pumps, e.g., progressive cavity pumps, piston pumps, peristaltic pumps, and the like. In a peristaltic pump, which is sometimes referred to as a hose pump, the fluid is contained within a flexible hose fitted inside the pump casing. The actual pumping operation, called peristalsis, is based on alternating compression and relaxation of the hose. Depending on the specific type of pump that may be used for each of the pump units 104a, 104b, and/or 104c, the pump may include a rotor with rollers, shoes, wipers or lobes mounted on the external circumference of the rotor. Typically, shoes are used in peristaltic hose pumps. The shoes compress the hose as the rotor rotates and passes along the length of the hose. Hose pumps, especially industrial strength hose pumps with circular pump casings, or circular hose pumps, may offer benefits in terms of measuring drilling fluid properties, as will be further explained below.

Hose pumps may be driven by variable speed motors, with the resulting flow being nearly directly proportional to the drive speed. A circular path taken by the interior hose of a circular hose pump may lead to reduced surging, as compared to a D-shaped path. Hose pumps in general are capable of pumping mineral slurry and have minimal restriction on particle size. Furthermore, hose pumps typically do not require gland water or dilution water. For the same pump rating, circular hose pumps are typically smaller and less costly than most comparable cylindrical progressive cavity pumps. While hose pumps may generally provide the above-listed beneficial design and operating characteristics, it should be understood that, as previously noted, other pump designs may be also used in the pump module 102.

In at least some embodiments, the suction ports 106a, 106b, 106c may be coupled to suction lines 112a, 112b, 112c. Similarly, the discharge ports 108a, 108b, 108c may be coupled to discharge lines 114a, 114b, 114c. Furthermore, as depicted in the illustrated embodiment of FIG. 1, the suction lines 112a, 112c may connect to a process stream, such as a mud treatment process stream or mud circulation process stream, and the suction line 112b may connect to a basin 116.

The system 100 may also include two riser pipes 118a, 118c, which may be substantially vertically oriented pipes. Although two riser pipes are shown, the system 100 may include only one pipe in at least some exemplary embodiments, whereas more than two riser pipes may be used in other embodiments. Also as shown in FIG. 1, in certain illustrative embodiments each of the two riser pipes 118a, 118c may be attached to a fluid analyzer system 162, as will be further described below. Additionally, pipe fittings 120a, 120c may be operatively coupled to the lower ends of the riser pipes 118a, 118c, which have bores that are in fluid communication with the bores of the riser pipes 118a, 118c, e.g., through the fluid analyzer system 162. Similarly, pipe fittings 122a, 122c may be attached to the upper ends of the riser pipes 118a, 118c, with bores that are also in fluid communication with the bores of the riser pipes 118a, 118c. In the illustrative embodiment shown in FIG. 1, the pipe fittings 120a, 120c are coupled to the discharge lines 114a, 114c, allowing the riser pipes 118a, 118c to receive discharged fluid from the pump units 104a, 104c.

In certain embodiments of the system illustrated in FIG. 1, pressure sensors 124a, 124c, 126a, 126c may be mounted on the pipe fittings 120a, 120c, 122a, 122c, with the sensitive parts of the sensors exposed to the bores of the pipe fittings 120a, 120c, 122a, 122c, thus enabling the pressure sensors 124a, 124c, 126a, 126c to measure pressure of fluids passing through the bores. In some embodiments, the pipe fittings 120a, 120c, 122a, 122c may be "T" fittings, and the pressure sensors 124a, 124c, 126a, 126c may be mounted on the branch legs of the fittings as shown in FIG. 1. In other embodiments, the pipe fittings 120a, 120c, 122a, 122c may be "Y" fittings, with the pressure sensors mounted on the angled flow legs of the "Y" fittings. Other shaped fittings may also be used.

As shown in FIG. 1, the pressure sensor 126a may be mounted on the pipe fitting 122a at a height difference 128a that is associated with the riser pipe 118a. Similarly, the pressure sensor 126c may be mounted on the pipe fitting 122c at a height difference 128c that is associated with the riser pipe 118c. The height differences 128a, 128c may be used in calculating fluid density of the sample drilling fluid moving through the system 100. In some exemplary embodiments, the height differences 128a, 128c may be the same, whereas in certain other embodiments the height differences 128a, 128c may be different. Moreover, the pressure sensors 124a, 124c may be positioned at the same or at different vertical heights relative to the system 100. Similarly, the pressure sensors 126a, 126c may also be positioned at the same or at different vertical heights.

The pump units 104a, 104c may be operated to continually discharge sample fluids into the riser pipes 118a, 118c. As the sample fluids pass through the riser pipes 118a, 118c, the pressure sensors 124a, 126a, 124c, 126c may be operated to measure the pressure of the fluids. The pressure difference between the pressure sensors 124a, 126a and the height difference 128a may then be used to determine the density of the fluid passing through the riser 118a, i.e., $\rho=\Delta P/(\Delta h \times g)$, where $\Delta P$ is pressure difference, $\Delta h$ is height difference, and g is acceleration due to gravity. Similarly, the pressure difference between the pressure sensors 124c, 126c and the height difference 128c may be used to determine the density of the fluid passing through the riser pipe 118c.

One possible benefit of the density measurement arrangement described above is that the fluid to be measured may be contained inside a vertical rise portion of a pipe where only the smallest of side flows can exist. As a result, pressure differences between the pressure sensors due to the effect of side flows may be substantially minimized, thereby potentially improving the accuracy of the measurements. Another possible benefit is that the deleterious effects that surge in feed pump flow can sometime have on measurements may be mitigated. For a fluid with a relatively low compressibility, such as, e.g., a drilling fluid, any surge sensed by the lower pressure sensors 124a, 124c will be almost immediately sensed by the upper pressure sensors 126a, 126c. Since the important parameter for density measurement is pressure difference along the riser pipe, and both pressure sensors on the riser pipe see approximately the same surge, the net effect of the surge on the measured pressure difference will be approximately zero.

As shown in FIG. 1, fluid lines 130a, 130c are coupled to the pipe fittings 122a, 122c. Additionally, fluid line 130a may be coupled to a fluid line 132a that leads to a feed port of a capillary rheometer 134 that is part of the system 100, and fluid line 130c may be coupled to a fluid line 132c that may lead to a process stream or elsewhere.

In the illustrated embodiment of FIG. 1, pump units 104a, 104c draw fluid from a process stream and discharge the fluid into the riser pipes 118a, 118c. The fluids passing through the riser pipes 118a, 118c may be the same or different. As the fluids pass through the riser pipes 118a, 118c, the pressure sensors 124a, 126a, 124c, 126c on the riser pipes 118a, 118c may be operated to measure pressure at the lower end and upper end of the riser pipes 118a, 118c and send pressure signals to an external control system (see, FIG. 3). The fluid from the riser pipe 118a then flows into capillary rheometer 134 and is discharged from the capillary rheometer 134 into a basin 116 through one or more capillary tubes 146 (one shown in FIG. 1). While the capillary tube 146 shown in FIG. 1 is illustrated as being substantially vertically oriented, i.e., such that the fluid in the capillary tube 146 flows substantially vertically downward, it should be understood by those of ordinary skill after a complete reading of the present disclosure that the capillary tubes 146 used in conjunction with any of the embodiments disclosed herein may be oriented so as to flow in substantially any direction, based on the specific requirements of the particular capillary rheometer 134. For example, in some embodiments the capillary tube(s) 146 may be oriented so that the fluid flows downward at an angle relative to vertical, whereas in other embodiments the capillary tube(s) 146 may be oriented so that the fluid flows substantially horizontally, flows upward at an angle relative to vertical, or flows substantially vertically upward. Pump 104b may be operated to draw fluid from the basin 116 and discharge the fluid into the discharge line 114b, which may lead to a process stream or elsewhere.

Figure 2A:
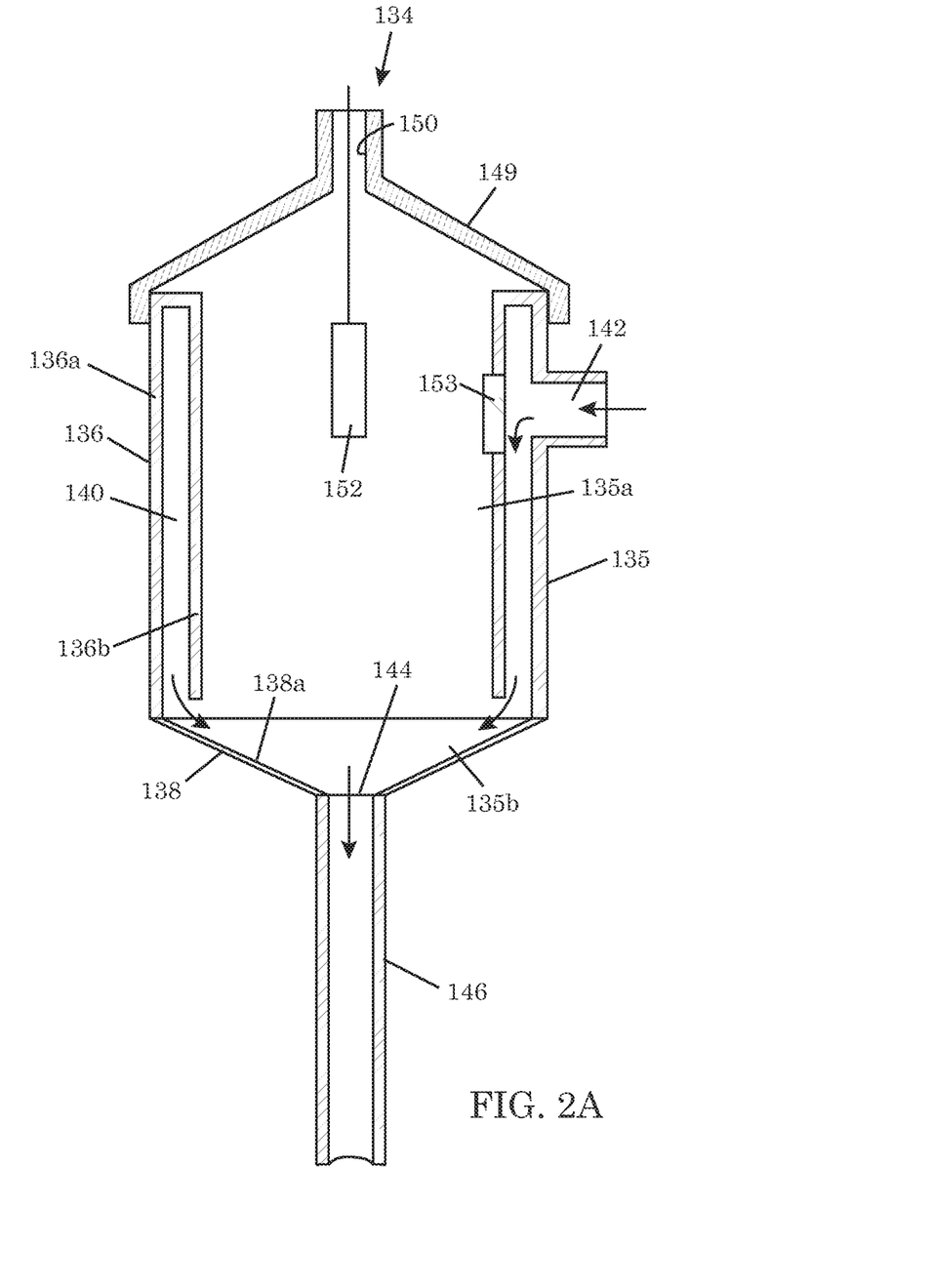
FIG. 2A shows a cross-section of a capillary rheometer with a level sensor.
Figure 3:
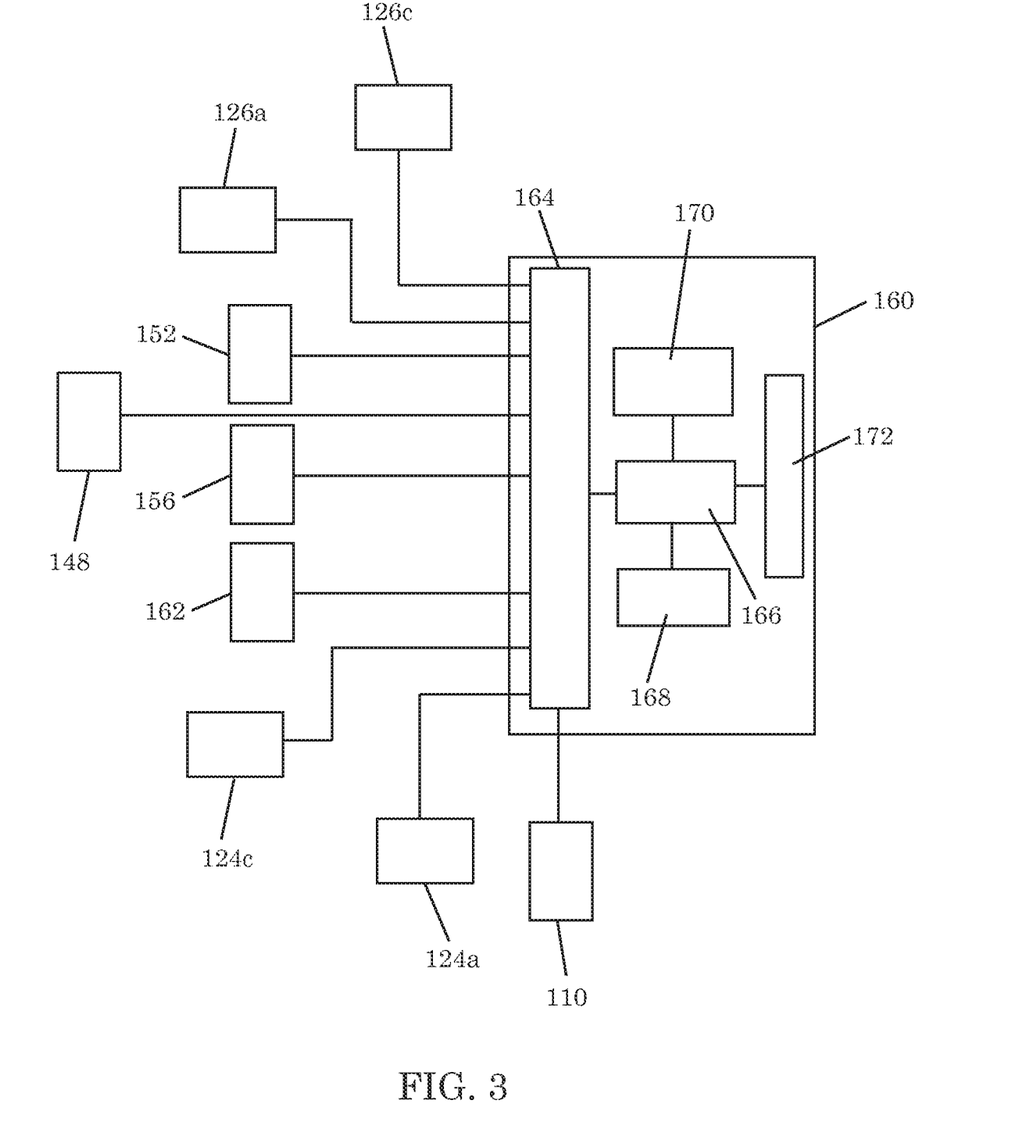
FIG. 3 shows a control system for the system of FIG. 1.

FIG. 2A shows one illustrative embodiment of the capillary rheometer 134 that is adapted to measure viscosity parameters, such as the viscosity parameters of drilling fluid, and the like. As will be further explained below, the measured viscosity parameters include at least the pressure drop and flow rate along a capillary tube. As shown in FIG. 2A, the capillary rheometer 134 may include a feed chamber 135 having a double wall providing an upper cavity 135a and a receptacle 138 providing a lower cavity 135b. In certain embodiments, the upper and lower cavities 135a, 135b may be substantially contiguous, in which case the cavities 135a, 135b may be considered as substantially one cavity. Furthermore, as shown in FIG. 2A, the double wall 136 may be made of an outer wall 136a and an inner wall 136b. The outer and inner walls 136a, 136b may be substantially concentric and spaced apart to define an annulus 140 therebetween. Typically, the outer and inner walls 136a, 136b and annulus 140 will be cylindrical in shape and/or circular in cross-section, although other shapes may also be used, e.g., square, rectangular, or oval cross-sections, and the like. The top of the annular gap 140 may be sealed by connecting or bridging the top ends of the outer and inner walls 136a, 136b. A feed port 142 may be formed in the outer wall 136a, through which fluid may be delivered to the annulus 140. The feed port 142 may be coupled to the fluid line 132a (in FIG. 1) to receive fluid from the riser pipe 118a (in FIG. 1). In certain embodiments, a wear plate 153 may also be mounted in the inner wall 136b opposite to the feed port 142, so that fluid entering the feed port 142 impinges on the wear plate 153 instead of directly on the inner wall 136b, thereby preventing excess wear of the inner wall 136b opposite to the feed port 142. In at least some exemplary embodiments, the wear plate 153 may be adapted to be removed and replaced through the upper cavity 135a, e.g., periodically as flow-induced wear on the wear plate 153 increases during the continued operation of the system 100.

The bottom of the outer wall 136a of the double wall 136 may be joined to the top of the receptacle 138, such that the annulus 140 may be open to the lower cavity 135b, thus allowing the fluid received in the annulus 140 to flow into the lower cavity 135b. The receptacle 138 may have a drain port 144 at a bottom end thereof. During operation of the capillary rheometer 134, fluid received in the lower cavity 135b may either rise into the upper cavity 135a and/or drain out of the lower cavity 135b through the drain port 144, depending on the rate at which the fluid is delivered to the feed port 142. As shown in FIG. 2A, a capillary tube 146 may be coupled to the drain port 144 to receive the fluid draining out of the lower cavity 135b. In one or more embodiments, the inner surface 138a of the receptacle 138 may be sloped, e.g., conical, to facilitate draining of fluid into the capillary tube 146. In some embodiments, the capillary tube 146 may have a high length-to-diameter ratio. For example, in one embodiment, the length-to-diameter ratio of the capillary tube 146 may be greater than 10, whereas in another embodiment, the length-to-diameter ratio may be greater than 100.

Figure 2B:
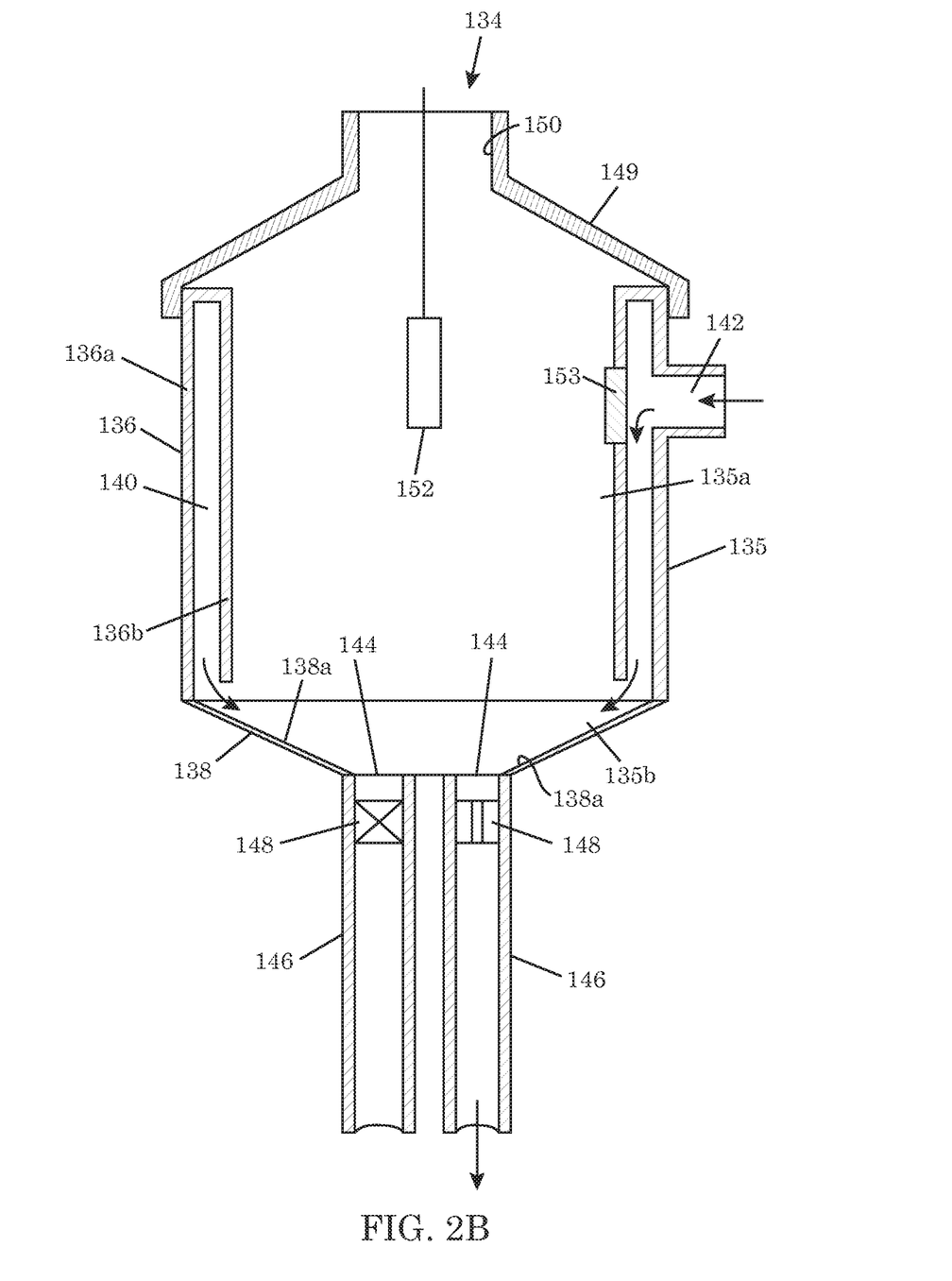
FIG. 2B shows a cross-section of a capillary rheometer with a plurality of capillary tubes.

In some embodiments, the receptacle 138 may have a plurality of drain ports, such as the drain port 144 of FIG. 2A. In such embodiments, a capillary tube, such as the capillary tube 146, may be coupled to each respective drain port 144. FIG. 2B shows an illustrative embodiment of the present disclosure wherein the receptacle 138 includes two drain ports 144, and wherein a capillary tube 146 is coupled to each respective drain port 144. It should be appreciated that the number of drain ports in FIG. 2B is exemplary only, as the receptacle 138 may have up to five or more drain ports 144 in other embodiments. As shown in FIG. 2B, flow control devices 148 may be arranged in each of the capillary tubes 146. The flow control devices 148 may be plugs or valves, and furthermore may also include actuators (not shown). In one or more embodiments, the actuators of the flow control devices 148 may be adapted to respond to external control signals and to perform one of two actions, e.g., to open so as to allow fluid to pass through a respective capillary tube 146, or to close so as to prevent fluid from passing through the capillary tube 146. Typically, the flow control devices 148 may be operated in a round-robin fashion, such that only one capillary tube 146 may be open for fluid flow during a given operation mode. The flow control devices 148 may also be selectively actuated based on a delivery rate of drilling fluid from the pump unit 104a (in FIG. 1). In at least some embodiments, each of the capillary tubes 146 may have different L/D ratios or geometries, where L is length and D is diameter, and each L/D ratio or geometry may be tailored to measure a particular range of viscosity parameters.

Returning to FIG. 2A, a cap 149 may be mounted on the feed chamber 135. The cap 149 may be adapted to prevent fluid from splashing out of the feed chamber 135. In some embodiments, the cap 149 may also have a vent hole 150 to allow for venting of air from the feed chamber 135 to the atmosphere. A level sensor 152 may also be inserted into the feed chamber 135 through the vent hole 150 or otherwise disposed in a suitable fashion, e.g., mounted, inside the feed chamber 135. The level sensor 152 may be adapted to measure the fluid level in the feed chamber 135. Furthermore, any suitable level sensor know in the art may be used. For example, in some embodiments, a non-contact level sensor, such as an ultrasonic level sensor, may be used for the level sensor 152. In operation, the ultrasonic level sensor is adapted to transmit and receive acoustic energy from the fluid surface, and to determine the level of the fluid from the received acoustic energy. In certain illustrative embodiments, the level sensor 152 may also be adapted to transmit level measurements to an external control system (see, FIG. 3), which may use the level measurements to control pump delivery rate to the feed port 142.

Figure 2C:
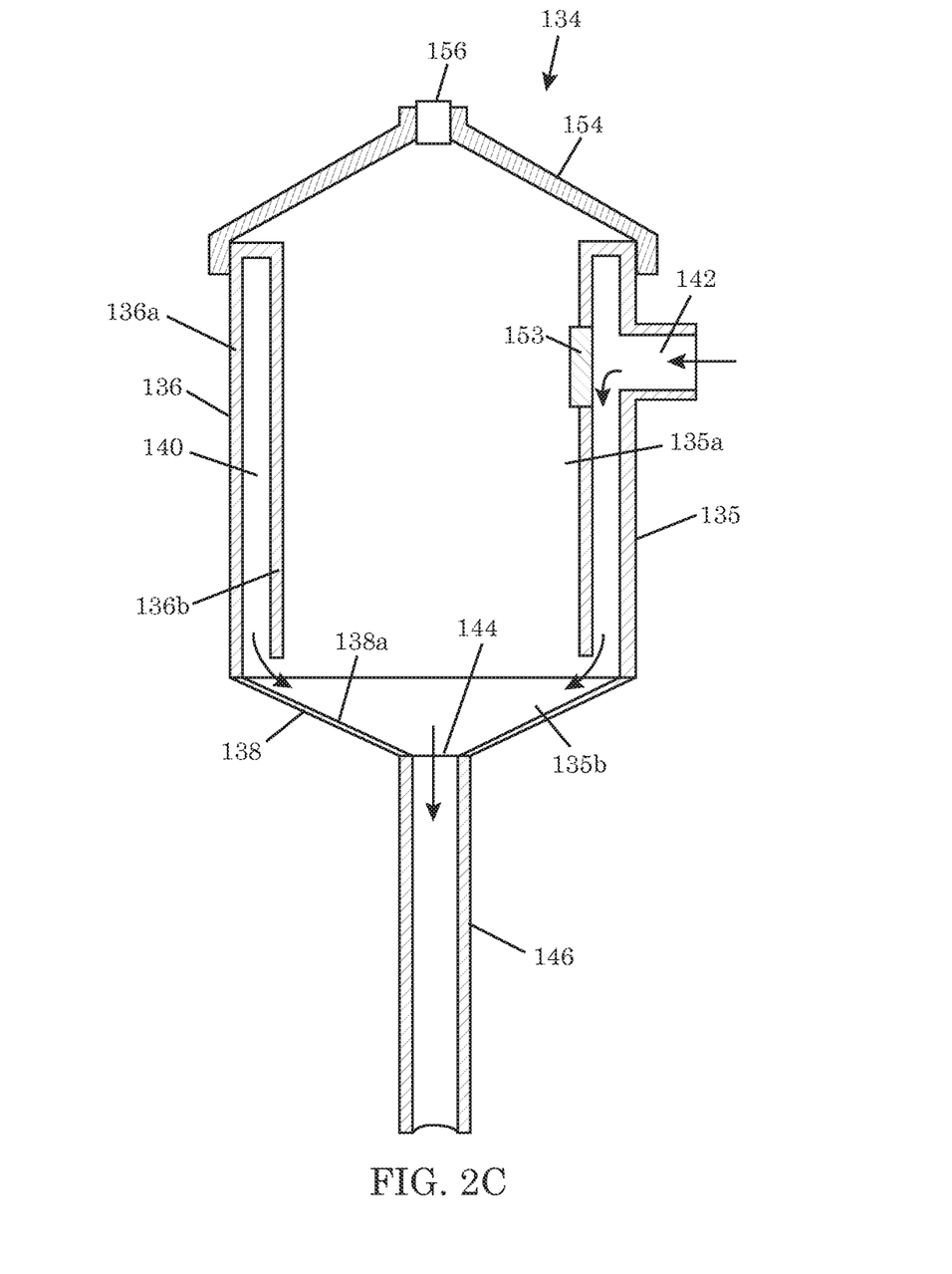
FIG. 2C shows a cross-section of a capillary rheometer with a pressure sensor.

FIG. 2C illustrates a further exemplary embodiment of capillary rheometers 134 shown in FIGS. 2A and 2B, wherein a differently configured cap 154 may be mounted on the feed chamber 135. As shown in FIG. 2C, the cap 154 does not include the open vent hole 150 of the FIG. 2A/2B embodiments, but instead, a pressure sensor 156 may be mounted in a hole at the top of the cap 154 such that the hole is sealed. The pressure sensor 156 may then measure the pressure in an air pocket above the fluid in the feed chamber 135, i.e., the fluid that is received through the feed port 142. In some embodiments, the pressure sensor 156 may be adapted to transmit pressure measurements to an external control system (see, FIG. 3), which may use the measurements to control the pump delivery rate to the feed port 142.

In some illustrative embodiments, the level sensor 152 (in FIG. 2A or 2B), or the pressure sensor 156 (in FIG. 2C), may be adapted to send measurement signals to an external control system (see, FIG. 3) during the operation of the system 100 (in FIG. 1). If the control system detects a spike, or increase, in the level measurement sent by the level sensor 152, or, alternatively, in the pressure measurement sent by the pressure sensor 156, the control system may infer that the capillary tube 146 (or an open capillary tube 146, in the case of a capillary rheometer 134 having a plurality of capillary tubes 146 such as shown in FIG. 2B) is beginning to clog, in which case the control system may send a resulting signal that triggers either a cleaning step or a warning alarm, or both.

In certain embodiments, the feed chamber 135 may have certain features that are adapted to facilitate an enhanced performance of the capillary rheometer 134 in measuring viscosity parameters. For example, one such feature is the double wall 136 that directs substantially all of the flow that is received at the feed port 142 to initially travel to the bottom of the upper cavity 135a. This flow pattern may mitigate any potential turbulence within the upper cavity 135a of the feed chamber 135 during operation of the capillary rheometer 134. The resulting reduction in the amount of turbulence—or even a complete lack of turbulence—within the feed chamber 135 may result in the upper surface of the fluid within the feed chamber 135 being substantially flat, which may subsequently allow for an improved target for a sonar level detector.

A further benefit that may be associated with the features of the feed chamber 135 is that incoming fluid kinetic energy may reduce, or even prevent, the settling of particles at the bottom of the receptacle 138. Such reduction in, or prevention of, particles from settling in the receptacle 138 may be beneficial because settled particles can often lead to two types of potential operational failures: (1) reduced flow from the feed chamber 135 into the capillary tube(s) 146, which may compromise measurement accuracy; and (2) blocked drain port(s) 144, such that fluid cannot flow into the capillary tube(s) 146. Yet another beneficial feature of the feed chamber 135 is the sloped, e.g., conical, surface 138a of the receptacle 138, which may assist in draining fluid into the capillary tube(s) 146. The sloped or conical surface may also reduce particle settling, and minimize feed chamber-to-capillary tube transition effects that can interfere with calibration of the capillary rheometer 134 for measuring viscosity parameters.

In one embodiment, the capillary rheometer 134 may be used to measure shear viscosity of drilling fluid. While the capillary rheometer 134 does not directly measure shear viscosity, the capillary rheometer 134 may be used to measure flow rate and pressure drop, which are parameters that can be converted to shear viscosity, as will be further explained below.

Viscosity is defined in terms of shear stress and strain rate, as follows:

$$\mu = \frac{\tau}{\dot{\gamma}} \qquad (1)$$

where:
μ is viscosity,
τ is shear stress existing between laminae of moving fluid, and
$\dot{\gamma}$ is strain rate between laminae of moving fluid.

To convert pressure drop and flow rate to viscosity, the Hagen-Poiseuille law may be used. For a pressure-driven flow through a circular tube, the Hagen-Poiseuille law states that:

$$Q = \frac{\pi R^4 \Delta P}{8\mu L} \qquad (2)$$

where:
μ is viscosity,
Q is volumetric flow rate,
R is tube radius,
ΔP is pressure drop, and
L is tube length.

In a laminar flow through a circular tube, a simple force balance shows that the shear stress at the wall of the tube is:

$$\tau = \frac{\Delta P R}{2L} \qquad (3)$$

From the Hagen-Poiseuille law in equation (2) and the definition of viscosity in equation (1), the strain rate at the wall of the tube is then given by:

$$\dot{\gamma} = \frac{4Q}{\pi R^3} \qquad (4)$$

The expressions (3) and (4) above are in terms of pressure drop, flow rate, and tube geometry. Pressure drop and flow rate can be obtained from capillary rheometer measurements, and tube geometry is known from the construction of the capillary rheometer. From these capillary rheometer data, shear stress and strain rate can be determined. Once the shear stress and strain rate are known, viscosity can be determined using equation (1).

The Hagen-Poiseuille law holds for steady, laminar, Newtonian flow. However, drilling fluid is commonly non-Newtonian and often non-laminar. The Hagen-Poiseuille equation has to be corrected to obtain the correct shear stress and strain rate for non-Newtonian and/or non-laminar flow. In particular, for non-laminar flow, the pressure drop, which affects shear stress, has to be corrected for entrance and exit effects at the capillary tube. Also, for non-Newtonian flow, the strain rate has to be corrected for non-Newtonian effects at the wall of the tube. Correction techniques such as the Bagley correction (for entrance and exit effects) and the Weissenberg-Rabinowitsch (for non-Newtonian effects) are known in the art and may be used. Another approach that may be used to correct or calibrate the Hagen-Poiseuille equation is described below.

In one embodiment, the Hagen-Poiseuille equation may be calibrated using measurements taken of drilling fluid having well known rheology behavior. In such embodiments, the calibration process begins by rearranging the Hagen-Poiseuille equation (2) using simple algebra:

$$\frac{8\mu}{\pi} = \frac{\Delta P R^4}{LQ} \quad (5)$$

To make use of sensor level data, pressure drop may be rewritten as follows:

$$\Delta P = \frac{\gamma}{h} \quad (6)$$

where:
γ is specific gravity of the fluid inside the feed chamber, and
h is the height of fluid inside the feed chamber.
Volumetric flow rate may be rewritten as follows:

$$Q = \frac{V}{t} \quad (7)$$

where:
V is volume of flow through the tube, and
t is time.
Equations (6) and (7) are then substituted into equation (5) to obtain:

$$\frac{8\mu}{\pi} = \frac{\gamma R^4 t}{hLV} \quad (8)$$

The natural logarithm of both sides of equation (8) are taken to obtain:

$$\ln\left(\frac{8\mu}{\pi}\right) = \ln\left(\frac{\gamma R^4 t}{hLV}\right) \quad (9)$$

The natural logarithm function is then distributed throughout the right side of equation (8) to obtain:

$$\ln\left(\frac{8\mu}{\pi}\right) = \ln(\gamma) + 4\ln(R) + \ln(t) - \ln(h) - \ln(L) - \ln(V) \quad (10)$$

The next step in the calibration process is to apply standard linear regression to equation (10) using a large number of data points collected by the capillary rheometer with a fluid having a known rheological behavior to obtain the coefficients that lead to the minimum least squares of error for the following relationship:

$$\ln\left(\frac{8\mu}{\pi}\right) = C + a1 \cdot \ln(\gamma) + a2 \cdot \ln(R) + \\ a3 \cdot \ln(t) - a4 \cdot \ln(h) - a5 \cdot \ln(L) - a6 \cdot \ln(V) \quad (11)$$

Next, the significance of each regression coefficient is tested using the standard t-test of the coefficients. Any unnecessary coefficients are removed.

The natural logarithm functions of expression (11) may then be disassembled using algebra to obtain:

$$\frac{8\mu}{\pi} = \frac{C\gamma^{a1} R^{a2} t^{a3}}{h^{a4} L^{a5} V^{a6}} \quad (12)$$

Coefficient C1 is defined as:

$$C_1 = \frac{\pi C}{8} \quad (13)$$

The definition of coefficient C1 from equation (13) is then applied to equation (12) to obtain the final relationship for viscosity:

$$\mu = \frac{C_1 \gamma^{a1} R^{a2} t^{a3}}{h^{a4} L^{a5} V^{a6}} \quad (14)$$

To determine the viscosity of drilling fluid using the capillary rheometer 134, drilling fluid may be pumped into the feed port 142 of the capillary rheometer 134. In one embodiment, the pump 104a (in FIG. 1) may pump the drilling fluid through the riser 118a (in FIG. 1) and into the feed port 142. From the feed port 142, the drilling fluid may then flow down the annulus 140 and into the receptacle 138. Thereafter, the fluid drains out of the drain port 144 at the bottom of the receptacle 138 and into the capillary tube 146 (or one of the capillary tubes 146, if the capillary rheometer 134 uses a plurality of capillary tubes 146 as shown in FIG. 2B).

As noted above, the capillary rheometer 134 may operate in a level mode (i.e., using the level sensor 152) or a pressure mode (i.e., using the pressure sensor 156) when measuring viscosity parameters. In one embodiment, e.g., in the level mode of operation, the upper surface of the drilling fluid in the feed chamber 135 is held substantially stationary at a specific level. The level sensor 152 may then continually measure the fluid level, and send appropriate signals to an external control system (see, FIG. 3), which may then use the transmitted fluid level signals to control the delivery rate or speed of the pump 104a (in FIG. 1). When the upper surface of the drilling fluid in the feed chamber 135 is substantially stable, the rate at which fluid flows through the capillary tube 146 is known, because it can be correlated to the pump speed. The pressure at the inlet to the capillary tube 146, or at the drain port 144, may then be determined from the height of the drilling fluid in the feed chamber 135 and the density of the fluid, which may be obtained from the measurements made along the riser 118a (in FIG. 1) with the pressure sensors 124a, 126a (in FIG. 1). Since the outlet or exit end of the capillary tube 146 is open to the atmosphere, the pressure drop along the capillary tube 146 will be the pressure at the inlet of the capillary tube 146. The flow rate through the capillary tube 146 and pressure drop along the capillary tube 146 may then be used to calculate viscosity of the drilling fluid in the manner described above.

In some embodiments, the pump speed may be adjusted to achieve a sequence of multiple, e.g., four or five, different stationary heights of the drilling fluid within the feed chamber, each of which correspond to different strain rates imparted to the drilling fluid. Each stationary height will yield different flow rate and pressure drop information. This permits the fluid viscosity to be measured over a relatively wide range of strain rates so that any non-Newtonian behavior of the drilling fluid may be captured and recorded.

In one embodiment, e.g., in the pressure mode, pressure at the inlet of the capillary tube 146, or at the drain port 144, may be held at a specific value by controlling the speed of the pump 104a (in FIG. 1). The pressure sensor 156 (in FIG. 2C) may then continually measure the pressure in the air pocket above the fluid in the feed chamber 135, and send appropriate signals to an external control system (see, FIG. 3), which may then use the transmitted pressure signals to control the pump speed. As in the previously described level mode embodiment, the rate at which fluid flows through the capillary tube 146 can be correlated to the pump speed. The pressure sensor 156 may provide a measure of the pressure at the inlet of the capillary tube 146, and the subsequently obtained flow rate and pressure information will allow viscosity of the drilling fluid to be determined.

FIG. 3 shows an external control system that may be used in conjunction with any of the illustrative embodiments described above and illustrated in FIGS. 1 and 2A-2C. In FIG. 3, a control system 160 may be operatively coupled to receive and send signals to the system 100 of FIG. 1. The control system 160 may communicate with the pressure sensors 124a, 126a, 124c, 126c on the riser pipes 118a, 118b. The control system 160 may further communicate with the controller of the drive motor 110 of the pump module. The control system 160 may also communicate with the level sensor 152 or pressure sensor 156, depending on the particular configuration of the capillary rheometer used. Additionally, the control system 160 may communicate with flow control device(s) 148 in the capillary tube(s) 146, depending on the particular configuration of capillary rheometer used. Furthermore, the control system 160 may also communicate with a fluid analyzer system 162, such as the fluid analyzer shown in FIG. 1, that is adapted to perform various fluid analyses as fluids pass through the riser pipes 118a, 118b, as will be described in further detail in conjunction with FIG. 4 below. The control system 160 may be implemented as a computer system, and may receive/send signals through a communications interface 164, which may use wired and/or wireless communications protocol. The control system 160 may further include a processor (or processors) 166, memory 168, display 170, and input interface (or device(s)) 172. The instructions for controlling operation of the system 100 may be stored in the memory 168, for example, or in another storage media accessible to the control system 160.

In one embodiment, the control system 160 may control the delivery rate of the pump units in the pump module (102 in FIG. 1). In those illustrative embodiment wherein the pump units (e.g., pump units 104a, 104b, 104c) are coupled to the same drive motor (e.g., drive motor 110), the delivery rates of the pump units may be the same, depending on the size and type of each pump unit 104a, 104b, and 104c. The delivery rate of the pump units 104a, 104b, and 104c, and particularly the pump unit feeding the capillary rheometer 134, may be selected to achieve a desired fluid level or inlet pressure at the capillary tube(s) 146, depending on which mode, e.g., level mode or pressure mode, the capillary rheometer 134 is operating in.

In another embodiment, the control system 160 may control the opening and closing off of flow in one or more of various capillary tubes 146 in those embodiments wherein the capillary rheometer 134 uses a plurality of capillary tubes 146 (e.g., as shown in FIG. 2B). The control system 160 may accomplish this by sending appropriate signals to the flow control devices (not shown) in each of the respective capillary tubes 146.

In a further embodiment, the control system 160 may receive fluid level information from the level sensor 152 associated with the feed chamber 135 (in FIGS. 2A and 2B), and use the level information to control the delivery rate of fluid from the pump module 102 to the capillary rheometer 134.

In yet another embodiment, the control system 160 may receive pressure information from the pressure sensor 156 associated with the feed chamber 135 (in FIG. 2C), and use the pressure information to control the delivery rate of fluid from the pump module 102 to the capillary rheometer 134.

In certain illustrative embodiments, the control system 160 may achieve multiple different flow rates at the capillary rheometer 134 by sending a pre-programmed set of electronic signals to control the operation of the pump (e.g., pump unit 104a) that feeds the capillary rheometer 146. Following is one illustrative example of controlling the capillary rheometer under multiple different flow rates.

Initially, the pump speed may be increased until the pump speed reaches a maximum value. When the pump speed reaches the maximum value, the control system 160 may then close the currently open capillary tube 146 by sending a signal to the appropriate flow control device 148, and open another capillary tube 146 having an alternate geometry that causes greater back pressure. Thereafter, the pump speed may be decreased until it reaches a minimum value. When the pump speed reaches the minimum value, the control system 160 may then close the currently open capillary tube 146 by sending a signal to the appropriate flow control device 148, and open another capillary tube 146 that has an alternate geometry that causes lesser back pressure. This sequence may be repeated until such time that all of the capillary tubes 146 have been opened at least once, or as necessary to accommodate achieving 4 or 5 levels or pressures for the drilling fluid being measured.

Figure 4:
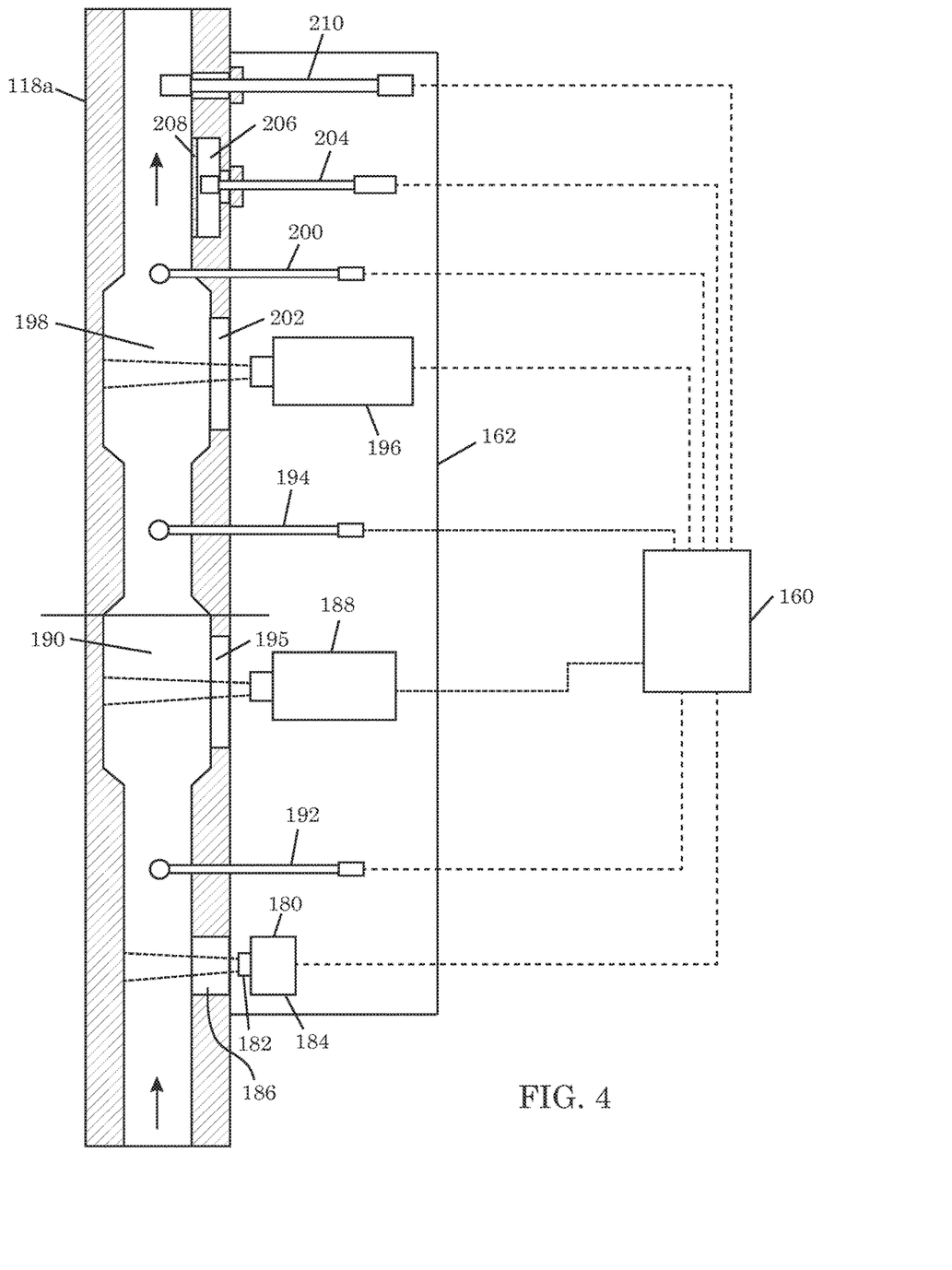
FIG. 4 shows a fluid analyzer system with a riser pipe.

Returning to FIG. 1, in some embodiments of the system 100, the composition of the fluids flowing therethrough may be analyzed as the fluids are flowing through the riser pipes 118a, 118b using one or more devices included in the fluid analyzer system 162. An illustrative embodiment of the fluid analyzer system 162 is shown in FIG. 4. It should be understood that only one half of the fluid analyzer system 162 is shown with respect to the riser pipe 118a, and that a fluid analyzer arrangement similar to the one shown in FIG. 4 may also be used for the riser pipe 118b.

In at least one embodiment, fluid analyzing may involve determining the mineral content of the fluids passing through the riser pipes 118a, 118b. For example, depending on the specific design of the fluid analyzer system 162, the mineral content determination may be made using X-ray fluorescence (XRF) spectroscopy, which is capable of detecting the type of minerals present in the fluids, as well as the concentration of the minerals in the fluids. The XRF method involves irradiating samples of the fluids with an X-ray beam. The excited fluids will emit X-rays that are characteristic of the elements present within the fluids. The emitted X-rays may then be detected and analyzed to determine the elements present within the fluids. Typically, only a few of the elements within the fluids need to be identified in order to infer the minerals that are present in the fluids. The table below shows examples of minerals typically found in drilling fluids and the corresponding elements that may be used to identify the minerals.

TABLE

| Mineral | Responsive Elements (in order of Fluorescence) |
| --- | --- |
| Barite | Barium, titanium, sulfur |
| Bentonite (or clays) | Silicon, aluminum, iron |
| Quartz | Silicon |

FIG. 4 shows an XRF spectrometer 180 arranged adjacent to the riser pipe 118a. The XRF spectrometer 180 has a radiation source 182 to provide the X-ray beam incident to the fluid in the riser pipe 118a and a XRF detector 184 to detect the emitted X-rays from the fluid. A window 186 made of material permeable to X-rays, such as Beryllium, may be formed in the wall of the riser pipe 118a. Alternatively, the riser pipe 118a may be made of a material permeable to X-rays. Any suitable commercially available or custom-built XRF spectrometer may be used as the XRF spectrometer 180. To analyze the fluids passing through both of the riser pipes 118a, 118b, it may be possible to irradiate both riser pipes 118a, 118b with a single radiation source and detect the emitted X-rays with two detectors. If necessary, the X-ray beam provided by the single radiation source may be directed to each pipe using suitable geometry, and each split will be directed to one of the riser pipes. For the embodiment shown in FIG. 4, the data collected by the detector 184 may be transmitted to the control system 160 for storage and further analysis.

In another illustrative embodiment, fluid analyzing may involve determining the liquid content of fluids passing through the riser pipes. For example, depending on the specific design of the fluid analyzer system 162, the liquid content determination may be made by separately irradiating the fluids in the riser pipes with microwaves and infrared radiation, and measuring the change in temperature of the fluids as a result of the separate radiations. The change in temperature due to irradiation with microwaves may provide an indication of the polar liquid content of the fluids, and the change in temperature due to irradiation with infrared may provide an indication of the total liquid content of the fluids.

FIG. 4 shows a microwave source 188 arranged adjacent to the riser pipe 118a, which is adapted to heat the fluid passing through a section 190 of the riser pipe. The section 190 is shaped in a way so as to allow a larger surface area of the fluid to be exposed to the radiation source, and may be fitted with a larger bore to allow the fluid flow to slow down as it passes through the section 190, thus allowing sufficient time for the fluid to be heated by the microwaves. Temperature sensors 192, 194 are arranged before and after the section 190 in order to determine the change in temperature of the fluid due to microwave heating. The wall of the riser pipe 118a may be provided with a window 195 in the section 190 that is permeable to microwaves. Alternately, the riser pipe 118a may be made of a material that is permeable to microwaves, but this may need to be coordinated with the material requirements for the XRF spectroscopy and infrared radiation.

An infrared source 196 may also be arranged adjacent to the riser pipe 118a, which may also be adapted to heat the fluid passing through a section 198 of the riser pipe. The section 198 is shaped in a way to allow a larger surface area of the fluid to be exposed to the radiation source, and may be fitted with a larger bore to allow the fluid flow to slow down as it passes through the section, thus allowing sufficient time for the fluid to be heated by the infrared radiation. A temperature sensor 200 is arranged after the section 198. The temperature sensors 194, 200 may be used to determine the change in temperature of the fluid as a result of infrared heating in the section 198. The wall of the riser pipe 118a may be provided with a window 202 in the section 198 that is permeable to infrared radiation. The infrared source 196 may be a heat lamp style light bulb or a laser diode or other suitable source of infrared radiation.

In the arrangement shown in FIG. 4, the fluid will flow through the microwave heated section 190 prior to flowing through the infrared heated section 198. The order of the radiation sources may be reversed in other embodiments such that infrared heating of the fluid occurs before microwave heating of the fluid.

From the measurements made using microwaves, the polar liquid content of the fluid passing through a riser pipe 118a may be determined. However, the amount of absorption of the microwave energy by the polar liquid depends on both the water content and the dissolved salt content. Therefore, in certain illustrative embodiments, the conductivity, conductance, or capacitance of the fluid may be used to resolve the disambiguation of the water and salt content. As shown in FIG. 4, a conductivity probe 204 may be used to determine the conductivity of the fluid passing through the riser pipe. In one embodiment, a chamber 206 may be formed in the wall of the riser pipe 118a, and a hydrophilic membrane 208 may be mounted between the bore of the riser pipe 118a and the chamber 206. The hydrophilic membrane 208 may thus allow only the water and salt phases of the fluid to flow into the chamber 206. The conductivity probe 204 may be inserted into the chamber 206, and may be adapted to measure only the conductivity of the water and salt phases. In such embodiments, the measured conductivity value may thus be proportional to the salt content in just the water phase.

In yet another illustrative embodiment, a pH measurement may also be made of the fluids passing through the riser pipe 118a. As shown in FIG. 4, a pH probe 210 may be inserted through the wall of the riser pipe 118a. Alternatively, the pH probe 210 may be mounted in a pipe fitting, such as a "T" fitting and the like, that is attached to the top of the riser pipe 118a, or between the riser pipe 118a and the pipe fitting 122a (in FIG. 1).

It should be appreciated that the various above-described devices of the fluid analyzer 162 may be arranged in a common housing, or alternatively in separate housings, and thereafter coupled to the respective riser pipes 118a, 118c so as to perform the requisite analyses of the fluids passing therethrough.

The particular embodiments disclosed above are illustrative only, as the invention may be modified and practiced in different but equivalent manners apparent to those skilled in the art having the benefit of the teachings herein. For example, the method steps set forth above may be performed in a different order. Furthermore, no limitations are intended to the details of construction or design herein shown. It is therefore evident that the particular embodiments disclosed above may be altered or modified and all such variations are considered within the scope and spirit of the invention.

What is claimed:

1. A system for measuring drilling fluid properties, comprising:
    a capillary rheometer that is adapted to measure viscosity parameters of drilling fluid,
        said capillary rheometer comprising:
            a feed chamber, said feed chamber comprising a cavity, at least a first drain port for draining fluid out of said cavity, a double wall defining an annulus that opens to said cavity, and a feed port in an outer portion of said double wall that is in fluid communication with said annulus; and
            at least a first capillary tube coupled to said at least said first drain port; and
    a pump that is adapted to pump fluid to said feed port.

2. The system of claim 1, wherein said feed chamber further comprises a receptacle joined to said double wall, said receptacle having a sloped inner surface that is adapted to facilitate draining of fluid from said cavity into said capillary tube.

3. The system of claim 1, wherein a length-to-diameter ratio of said capillary tube is greater than 10.

4. The system of claim 1, wherein a length-to-diameter ratio of said capillary tube is greater than 100.

5. The system of claim 1, wherein said feed chamber further comprises at least a second drain port, said capillary rheometer further comprising at least a second capillary tube coupled to said at least said second drain port, wherein each of said first and second capillary tubes has a geometry selected for measuring a different range of viscosity parameters.

6. The system of claim 5, further comprising a flow control device fitted in each of said first and second capillary tubes, wherein each of said flow control devices is adapted control a flow of fluid through a respective capillary tube.

7. The system of claim 6, wherein each flow control device is responsive to an external control signal.

8. The system of claim 1, further comprising at least one sensor for measuring at least one of a fluid level and pressure in said feed chamber.

9. The system of claim 8, further comprising a cap for covering said feed chamber, wherein said cap comprises a vent hole formed therein for venting said feed chamber to atmosphere.

10. The system of claim 1, wherein said pump is a positive displacement pump.

11. The system of claim 10, wherein said pump is a peristaltic hose pump.

12. The system of claim 1, further comprising at least one riser pipe having an inlet end in fluid communication with a discharge port of said pump.

13. The system of claim 12, wherein an outlet end of said at least one riser pipe is in fluid communication with said feed port of said capillary rheometer.

14. The system of claim 12, further comprising a pair of pressure sensors mounted in fixed relation to said at least one riser pipe, wherein a first one of said pair of pressure sensors is separated from a second one of said pair of pressure by a vertical distance, each of said pair of pressure sensors being adapted to measure pressure of fluid flowing through said at least one riser pipe.

15. The system of claim 12, further comprising a fluid analysis device coupled to said at least one riser pipe, said fluid analysis device being adapted to measure at least one parameter related to a composition of said fluid flowing through said at least one riser pipe.

16. The system of claim 15, wherein said fluid analysis device comprises an X-ray spectrometer arranged adjacent to an X-ray section of said at least one riser pipe, wherein said X-ray spectrometer is adapted to excite fluid flowing through said X-ray section with an X-ray beam and to receive excited X-rays from said fluid.

17. The system of claim 16, wherein said X-ray section is transparent to X-rays.

18. The system of claim 15, wherein said fluid analysis device comprises at least one of a microwave source arranged adjacent to a microwave transparent section of said at least one riser pipe and an infrared source arranged adjacent to an infrared transparent section of said at least one riser pipe, said microwave source being adapted to heat fluid passing through said microwave transparent section and said infrared source being adapted to heat fluid passing through said infrared transparent section.

19. The system of claim 18, wherein said fluid analysis device further comprises at least two temperature sensors that are adapted to measure a change in fluid temperature of fluid flow through said at least one riser pipe.

20. The system of claim 15, wherein said fluid analysis device comprises a probe that is adapted to measure at least one of a conductivity, a conductance, and a capacitance of fluid flowing through said at least one riser pipe.

21. The system of claim 20, wherein said fluid analysis device comprises a hydrophilic membrane covering a fluid filled chamber, said probe being operatively coupled to said fluid filled chamber.

22. The system of claim 15, wherein said fluid analysis device comprises a pH probe that is adapted to measure a pH of fluid flowing through said at least one riser pipe.

23. A method of measuring drilling fluid properties, the method comprising:
    pumping drilling fluid into a feed chamber of a capillary rheometer, said feed chamber comprising a cavity and a double wall defining an annulus that opens to said cavity;
    controlling a delivery rate of said drilling fluid into said feed chamber during said pumping such that a first strain rate is imparted to said drilling fluid flowing through said capillary rheometer;
    draining said drilling fluid from said cavity through at least one drain port of said feed chamber and into an inlet of a capillary tube coupled to said at least one drain port;
    determining a flow rate and a pressure drop of said drilling fluid flowing through said capillary tube for said first strain rate; and
    determining a viscosity of said drilling fluid from said flow rate and said pressure drop.

24. The method of claim 23, wherein determining said viscosity of said drilling fluid comprises calibrating the Hagen-Poiseuille equation to account for non-Newtonian and non-laminar fluid effects and determining said viscosity using said calibrated Hagen-Poiseuille equation.

25. The method of claim 24, wherein said calibrated Hagen-Poiseuille equation has the form:

$$\mu = \frac{C_1 \gamma^{a1} R^{a2} t^{a3}}{h^{a4} L^{a5} V^{a6}}$$

wherein $\mu$ is viscosity, $\gamma$ is specific gravity of the fluid inside the feed chamber, R is radius of the capillary tube, t is time require for a volume of fluid to pass through the capillary tube, h is height of the fluid inside the feed chamber, L is length of the capillary tube, V is volume of fluid passing through the capillary tube during time t, and C, $C_1$, a1, a2, a3, a4, a5, and a6 are coefficients determined from applying regression analysis to a set of data collected by the capillary rheometer with a fluid having a known rheological behavior.

26. The method of claim 23, wherein said delivery rate is controlled such that an upper surface of said drilling fluid in feed chamber is held substantially stationary at a first level within the feed chamber.

27. The method of claim 26, wherein controlling said delivery rate comprises receiving a signal from a level sensor arranged to measure a level of said upper surface of said drilling fluid and using said level sensor signal to control a rate of said pumping.

28. The method of claim 26, further comprising adjusting said delivery rate to achieve a sequence of multiple different levels of said drilling fluid, each of said sequence of multiple different levels corresponding to a respective different strain rate imparted to said drilling fluid flowing through said capillary rheometer, and determining a flow rate and a pressure drop and a viscosity for each respective different strain rate.

29. The method of claim 23, wherein said delivery rate is controlled such that pressure of the drilling fluid is held at a substantially constant first pressure at the inlet of the capillary tube.

30. The method of claim 29, wherein controlling said delivery rate comprises receiving a signal from a pressure sensor arranged to measure pressure in an air pocket above an upper surface of said drilling fluid within said feed chamber and using said pressure sensor signal to control a rate of said pumping.

31. The method of claim 29, further comprising adjusting said delivery rate to achieve a sequence of multiple different pressures of said drilling fluid at said inlet of said capillary tube, each of said sequence of multiple different pressures corresponding to a respective different strain rate imparted to said drilling fluid flowing through said capillary rheometer, and determining a flow rate and a pressure drop and a viscosity for each respective different strain rate.

32. The method of claim 23, further comprising draining said drilling fluid through a plurality of drain ports into respective inlets of a plurality of capillary tubes coupled to each of said plurality of drain ports, and selectively opening or closing each respective drain port and adjusting said delivery rate of said drilling fluid into said feed chamber to achieve a sequence of multiple different strain rates imparted to said drilling fluid flowing through said capillary rheometer.

33. The method of claim 23, wherein pumping said drilling fluid comprises receiving said drilling fluid from a mud treatment process stream or a mud circulation process stream.

34. The method of claim 23, further comprising pumping said drilling fluid into at least one riser pipe, measuring a difference in pressure between two locations vertically spaced apart on said at least one riser pipe, and determining a density of said drilling fluid using said pressure difference and a vertical height difference between said two locations.

35. The method of claim 34, wherein pumping said drilling fluid into said feed chamber comprises pumping said drilling fluid through said at least one riser pipe into said feed chamber.

36. The method of claim 35, wherein determining said viscosity further comprises using said determined density of said drilling fluid.

37. The method of claim 34, further comprising exposing said drilling fluid passing through a section of said at least one riser pipe to microwave energy, measuring a change in temperature of said drilling fluid as a result of said exposure to said microwave energy, and determining a polar liquid content of said drilling fluid from said change in temperature.

38. The method of claim 34, further comprising measuring at least one of a conductivity, a conductance, and a capacitance of said drilling fluid passing through said at least one riser pipe.

39. The method of claim 38, wherein measuring said at least one of said conductivity, said conductance, and said capacitance of said drilling fluid comprises measuring at least one of conductivity, a conductance, and a capacitance of a hydrophilic content of said drilling fluid, and further comprising determining a water content of said drilling fluid using said at least one of said conductivity, said conductance, and said capacitance of said hydrophilic content of said drilling fluid and said polar liquid content of said drilling fluid.

40. The method of claim 34, further comprising exposing said drilling fluid passing through a section of said at least one riser pipe to infrared radiation, measuring a change in temperature of said drilling fluid as a result of said exposure to said infrared radiation, and determining a total liquid content of said drilling fluid from said change in temperature.

41. The method of claim 34, further comprising measuring a pH of said drilling fluid passing through said at least one riser pipe.

42. The method of claim 34, further comprising exposing said drilling fluid passing through a section of said at least one riser pipe to an X-ray beam, detecting emitted X-rays from said drilling fluid, and analyzing said detected X-rays to determine a mineral content of said drilling fluid.

* * * * *

UNITED STATES PATENT AND TRADEMARK OFFICE
CERTIFICATE OF CORRECTION

| | |
|---|---|
| PATENT NO. | : 9,513,272 B2 |
| APPLICATION NO. | : 14/203854 |
| DATED | : December 6, 2016 |
| INVENTOR(S) | : Larson |

It is certified that error appears in the above-identified patent and that said Letters Patent is hereby corrected as shown below:

In the Claims

Column 20, Line 30 Claim 38, Line 1, change "claim 34" to -- claim 37 --.

Signed and Sealed this
Seventh Day of March, 2017

Michelle K. Lee
*Director of the United States Patent and Trademark Office*